United States Patent
Haden et al.

(10) Patent No.: US 10,345,229 B2
(45) Date of Patent: Jul. 9, 2019

(54) FURNACE ATMOSPHERE MEASUREMENT

(71) Applicant: PILKINGTON GROUP LIMITED, Lathom (GB)

(72) Inventors: Michael Richard Haden, St. Helens (GB); Julian Inskip, Helsby (GB); William Stephen Perry, Stockport (GB); Ian Ross Williams, Parbold (GB)

(73) Assignee: Pilkington Group Limited, Lathom (GB)

( * ) Notice: Subject to any disclaimer, the term of this patent is extended or adjusted under 35 U.S.C. 154(b) by 134 days.

(21) Appl. No.: 15/506,276

(22) PCT Filed: Aug. 27, 2015

(86) PCT No.: PCT/GB2015/052479
§ 371 (c)(1),
(2) Date: Feb. 24, 2017

(87) PCT Pub. No.: WO2016/034858
PCT Pub. Date: Mar. 10, 2016

(65) Prior Publication Data
US 2017/0254744 A1 Sep. 7, 2017

(30) Foreign Application Priority Data
Sep. 1, 2014 (GB) .................................. 1415435.5

(51) Int. Cl.
*G01N 21/31* (2006.01)
*G01J 3/42* (2006.01)
(Continued)

(52) U.S. Cl.
CPC .......... *G01N 21/314* (2013.01); *G01J 3/0218* (2013.01); *G01J 3/0286* (2013.01);
(Continued)

(58) Field of Classification Search
CPC .................................................... G01N 21/314
(Continued)

(56) References Cited

U.S. PATENT DOCUMENTS

| 4,820,046 A * | 4/1989 | Sohma .................. G01J 3/2823 |
| | | 356/315 |
| 5,042,946 A * | 8/1991 | Harada ............... G01N 21/3103 |
| | | 356/307 |

(Continued)

FOREIGN PATENT DOCUMENTS

| EP | 0682245 A | 11/1995 |
| EP | 2693203 A1 | 2/2014 |

*Primary Examiner* — Tarifur R Chowdhury
*Assistant Examiner* — Omar H Nixon
(74) *Attorney, Agent, or Firm* — Marshall & Melhorn, LLC

(57) ABSTRACT

A method of determining the concentration of a species in a portion of a furnace atmosphere is described. The method comprises the steps of measuring first, second and third intensities of electromagnetic radiation in the furnace at first, second and third wavelengths respectively. The third wavelength is selected to be representative of absorption of electromagnetic radiation by the species. A fourth intensity of electromagnetic radiation is calculated, being an estimate of the intensity of electromagnetic radiation in the furnace at the third wavelength absent any absorbing species in the furnace atmosphere. The third intensity and the fourth intensities are used to determine a parameter that is proportional to the concentration of absorbing species in the portion of the furnace atmosphere. Apparatus for carrying out the method is also described.

20 Claims, 4 Drawing Sheets

(51) Int. Cl.
*G01J 3/02* (2006.01)
*G01N 21/85* (2006.01)

(52) U.S. Cl.
CPC ........ *G01J 3/42* (2013.01); *G01N 2021/3148* (2013.01); *G01N 2021/3155* (2013.01); *G01N 2021/8578* (2013.01)

(58) Field of Classification Search
USPC .......................................................... 356/315
See application file for complete search history.

(56) References Cited

U.S. PATENT DOCUMENTS

| | | | | |
|---|---|---|---|---|
| 5,239,185 | A * | 8/1993 | Ito | G01N 21/39 250/226 |
| 5,920,388 | A * | 7/1999 | Sandberg | G01N 15/0205 356/315 |
| 6,084,661 | A * | 7/2000 | Mendelson | G01N 21/314 250/343 |
| 6,222,626 | B1 * | 4/2001 | Radziuk | G01N 21/3103 356/307 |
| 2004/0157341 | A1 * | 8/2004 | Reynolds | A61B 5/14532 356/39 |
| 2005/0173635 | A1 * | 8/2005 | Smith | G01N 21/3504 250/339.13 |
| 2007/0052965 | A1 * | 3/2007 | Pesach | G01N 21/1702 356/432 |
| 2011/0301910 | A1 | 12/2011 | Spellicy | |
| 2014/0192342 | A1 * | 7/2014 | Sass | G01N 33/491 356/40 |
| 2015/0021482 | A1 * | 1/2015 | Muller | G01N 15/0205 250/341.1 |

* cited by examiner

FURNACE ATMOSPHERE MEASUREMENT

BACKGROUND OF THE INVENTION

The present invention relates to a method and apparatus for measuring a concentration of a species in a portion of an atmosphere of a furnace, in particular a concentration of an alkali metal species (such as sodium) in a portion of the atmosphere of a glass making furnace.

It is known that alkali vapour, in particular sodium, plays an important role in the corrosion behaviour of refractory materials used in glass making furnaces.

Methods are known using extractive sampling to determine the level of sodium in the atmosphere, but such methods are time consuming and do not provide continuous monitoring.

Methods are also known using laser induced breakdown spectroscopy. Such systems are expensive and require high power lasers.

It is also known to use the absorption of visible light traversing the furnace atmosphere to measure the absorption due to sodium atoms. Such a system requires two holes in the furnace (one in each opposing sidewall) and as such increases the likelihood of cold air ingress into the furnace. Also it can be difficult to accurately align the light source with the detector.

There is therefore a need for a method for determining the concentration of sodium that may be in a furnace atmosphere that at least partially overcomes the above problems.

SUMMARY OF THE INVENTION

Accordingly the present invention provides a method of determining the concentration of a species in a portion of a furnace atmosphere, the species absorbing electromagnetic radiation inside the furnace, the method comprising the steps:

(i) measuring a first intensity $I_1$ of electromagnetic radiation in the furnace at a first wavelength $\lambda_1$;
(ii) measuring a second intensity $I_2$ of electromagnetic radiation in the furnace at a second wavelength $\lambda_2$;
(iii) measuring a third intensity $I_3$ of electromagnetic radiation in the furnace at a third wavelength $\lambda_3$; the third wavelength being selected to be representative of the absorption of electromagnetic radiation in the furnace by the species;
(iv) calculating a fourth intensity $I_4$ at the third wavelength using the first and second intensities, the fourth intensity being an estimate of the intensity of electromagnetic radiation in the furnace at the third wavelength absent any species in the furnace atmosphere that absorbs electromagnetic radiation at the third wavelength; and
(v) using the third intensity and the fourth intensity to determine a parameter that is proportional to the concentration of the absorbing species in the portion of the furnace atmosphere.

In contrast to spectrophotometric methods that first require the measurement of a wavelength dependent background spectrum to correct subsequent measurements, the present invention is self calibrating and does not require a separate background trace to be run. This has the advantage of speeding up the measurements and each measurement is effectively taken with an instantaneous background reading compared to a background trace that may have been taken many reading ago.

Typically a furnace is a box-like construction having four walls, a bottom and a roof, each made of suitable materials, such as refractory materials. Material contained in the furnace partially fills the furnace. The furnace atmosphere is above the material contained within the furnace.

The concentration of the absorbing species in the portion of the furnace atmosphere may be the same as the concentration of the absorbing species in the entire furnace atmosphere.

The concentration of the absorbing species in the entire atmosphere of the furnace may vary at different positions above the material in the furnace, for example due to temperature variations.

Preferably the first wavelength is selected such that the intensity measurement at the first wavelength is the same, or substantially the same, as the intensity measurement at the first wavelength if there were no absorption of electromagnetic radiation due to the species.

Preferably the second wavelength is selected such that the intensity measurement at the second wavelength is the same, or substantially the same, as the intensity measurement at the second wavelength if there were no absorption of electromagnetic radiation due to the species.

Suitably the first and/or second wavelengths are selected such that the difference between the intensity measurement at the first and/or second wavelengths when the species are in the portion of the furnace atmosphere compared to the intensity measurement at the first and/or second wavelengths when there are no species in the portion of the furnace atmosphere is low, preferably less than 10%, more preferably less than 5%, or 4%, or 3%, or 2%, or 1%.

In principle it is possible to determine the temperature inside the furnace and then to calculate a black body spectrum based on that temperature. It is then possible to subtract the calculated black body intensity from the measured intensity to obtain a response due to the absorbing metal species. In practise however it can be difficult to accurately determine the temperature inside the furnace, with a subsequent impact on the accuracy of the measurement.

The present inventors have found that by making a measurement of the intensity of electromagnetic radiation in the furnace at two or more wavelengths it is not necessary to measure the temperature inside the furnace.

The present invention provides a method for determining the concentration of a species in a portion of the furnace atmosphere that absorbs electromagnetic radiation inside the furnace. Typically the species is a metal species, in particular an alkali metal species, although the species may be any other species that may absorb electromagnetic radiation inside the furnace, for example hydroxyl groups, boron or selenium. Measurement wavelengths may be suitably chosen depending upon the particular species and a suitable measurement device may be used for measuring the intensity of electromagnetic radiation inside the furnace at the suitably chosen measurement wavelengths.

Preferably steps (i), (ii) and (iii) are carried out at the same time. Using a suitably configured spectrometer it is possible to measure all the intensities at the same time.

Preferably step (iii) is carried out after step (ii) and after step (i). Preferably step (ii) is carried out after step (i) and before step (iii).

Preferably at step (v) the parameter is determined using the difference between the third intensity and the fourth intensity, for example $I_3 - I_4$.

The measurement steps (i), (ii) and (iii) are preferably taken at the same position (a measuring position) within the furnace. At the measuring position the absorption of electromagnetic radiation by the species in the furnace atmosphere depends upon the path length over which the electromagnetic radiation has travelled. That is, during the measurement steps (i), (ii) and (iii) the respective intensity is measured through a measurement path length.

Preferably the first, second and third intensities are corrected for the measurement path length, suitably by using the Lambert-Beer Law.

Preferably during step (v) the third and fourth intensity are corrected for the measurement path length, suitably by using the Lambert-Beer Law.

Preferably during step (v) the parameter is corrected for the measurement path length, suitably by using the Lambert-Beer Law.

The Lambert-Beer Law can be written as:

$$I_\lambda = I_0 e^{-k\alpha\lambda l} \quad (1)$$

wherein $I_\lambda$ is the incident intensity at a particular wavelength $\lambda$ i.e. the first measured intensity at the first wavelength, $I_0$ is the background intensity at that wavelength i.e. the predicted intensity at the third wavelength, k is the concentration of electromagnetic radiation absorbing species in ppm, l is the path length in meters (m) through the medium, and $\alpha$ is the absorption coefficient (in $ppm^{-1}\, m^{-1}$) of the absorbing species at the particular wavelength $\lambda$.

For example, if the measuring position is at a location x, y in the furnace (in relation to a fixed datum in the furnace), and the measurements of intensity are made by viewing along a straight line l-l', the line l-l' starting at the position x, y and ending at the position X, Y (measured relative to the same fixed datum in the furnace), then the measurement path length is the length of the straight line l-l'. Suitably the measurement path length ends at a point on one of the furnace walls. Suitably the measurement path length is perpendicular, or substantially perpendicular to one of the furnace walls, for example a side wall or an end wall.

The absorption coefficient for the species at the third wavelength can be determined by suitably correlating the intensity response at the third wavelength against the concentration of species having been determined by some other technique, for example extractive sampling. If necessary the concentration of species determined by the other technique may be suitably adjusted to take into account the possibility that the species may be in different forms and/or redox states. The temperature dependent equilibrium concentrations for the different forms of the species can be calculated using thermodynamic techniques known to a person skilled in the art.

The parameter may be used to determine a qualitative concentration of the species in the portion of the furnace atmosphere or a quantitative concentration of the species in the portion of the furnace atmosphere.

When the concentration is qualitative it is possible to use the method to determine relative changes in the concentration of the species in the portion of the furnace atmosphere. When the concentration is quantitative an absorption coefficient at the third wavelength for the particular species is needed to determine the concentration of that species in the portion of the furnace atmosphere.

In some embodiments the first and second intensities ($I_1$, $I_2$) are used to determine the temperature inside the furnace. The temperature of the measurement can then be determined by calculating the gradient $\delta I/\delta\lambda$ and comparing the calculated gradient with the theoretical gradient at that wavelength, assuming a blackbody radiation source. The determined temperature can be used to calculate a blackbody spectrum, thereby allowing a calculation of an intensity at the third wavelength. The measured intensity at the third wavelength may then be subtracted from the calculated blackbody intensity at that wavelength.

In other embodiments the fourth intensity is calculated by linear interpolation between the first intensity at the first wavelength and the second intensity at the second wavelength to obtain a predicted intensity at the third wavelength, the predicted intensity at the third wavelength being the intensity of electromagnetic radiation at the third wavelength absent any species that absorb electromagnetic radiation at the third wavelength that are in the portion of the furnace atmosphere.

Other embodiments have other preferable features.

Preferably the first wavelength and the second wavelength are shorter than the third wavelength.

Preferably the first wavelength is shorter than the third wavelength and the second wavelength is longer than the third wavelength.

In some embodiments, the first wavelength and/or the second wavelength and/or the third wavelength is/are in the ultraviolet region of the electromagnetic radiation spectrum.

In some embodiments, the first wavelength and/or the second wavelength and/or the third wavelength is/are in the visible region of the electromagnetic radiation spectrum.

In some embodiments, the first wavelength and/or the second wavelength and/or the third wavelength is/are in the infra red region of the electromagnetic radiation spectrum.

In some embodiments at least a portion of the electromagnetic radiation in the furnace has a wavelength between 400 nm and 800 nm. That is, there is a spectral distribution of electromagnetic radiation in the furnace between 400 nm and 800 nm.

In a preferred embodiment the species is a metal species. Preferably the metal species is an alkali metal species, more preferably sodium, most preferably sodium atoms.

When the metal species is sodium, preferably the third wavelength is between 585 nm and 595 nm, more preferably between 588 nm and 591 nm, even more preferably a sodium D-line, most preferably 589.3 nm.

When the metal species is sodium, preferably the first wavelength is between 500 nm and 584.9 nm, preferably between 500 nm and 575 nm, more preferably between 565 nm and 575 nm.

When the metal species is sodium, preferably the second wavelength is between 500 nm and 584.9 nm, preferably between 575.1 nm and 584.9 nm, more preferably between 578 nm and 584 nm.

When the metal species is sodium, preferably the second wavelength is between 596 nm and 700 nm.

When the metal species is sodium, the sodium species in the furnace atmosphere may exist in at least the form of elemental sodium and sodium hydroxide. Preferably the ratio of sodium hydroxide to sodium is determined for a given measurement temperature to provide a determination of the concentration of sodium and sodium hydroxide in the furnace atmosphere. For example, if the ratio of sodium to sodium hydroxide (moles sodium/moles sodium hydroxide) in the furnace atmosphere at a temperature T is r, then the concentration of sodium hydroxide in the furnace atmosphere can be determined following step (v). That is, following suitable correction for the measurement path length, if the concentration of sodium is determined to be S, then the concentration of sodium hydroxide is S/r. The total concentration of sodium species in the furnace atmosphere can then be calculated and compared with other measurement techniques, for example extractive sampling.

In some embodiments, the furnace is a glass making furnace, preferably a furnace making soda-lime-silica glass.

A typical soda-lime-silica glass composition is (by weight), $SiO_2$ 69-74%; $Al_2O_3$ 0-3%; $Na_2O$ 10-16%; $K_2O$ 0-5%; MgO 0-6%; CaO 5-14%; SO3 0-2%; $Fe_2O_3$ 0.005-2%. The glass may also contain other additives, for example, refining aids, which would normally be present in an amount of up to 2%. The soda-lime-silica glass composition may contain other colouring agents such as $Co_3O_4$, NiO and Se.

The furnace may be a furnace making a borosilicate glass.

Other embodiments have other preferable features.

Preferably the measured intensity at two or more wavelengths is used to determine the intensity at the third wavelength. Using more intensity measurements at more wavelengths allows more complex interpolation schemes to calculate the fourth intensity.

Preferably the furnace is a glass container making furnace or a glass sheet making furnace, such as a furnace for feeding molten glass to a float bath or between a pair of rollers.

There may be a different concentration of the species in different portions of the atmosphere of the furnace, for example at different locations in the furnace that are at different temperatures. The method may be used to determine the concentration of the species in two or more portions of the furnace atmosphere. The method may be used to build up a concentration map of the species in the furnace atmosphere.

From a second aspect the present invention provides an apparatus for measuring the concentration of a species in a portion of a furnace atmosphere, the species absorbing electromagnetic radiation in the furnace, the apparatus comprising:

collection means for collecting electromagnetic radiation from inside the furnace;

coupling means for directing the collected light to a suitable measuring means, the measuring means being configured to measure the intensity of the collected electromagnetic radiation at one or more wavelengths; and computing means, in particular a computer, configured to take the output from the measuring means to determine the amount of absorption of electromagnetic radiation inside the furnace at a measurement wavelength, the measurement wavelength being selected to be representative of the absorption of electromagnetic radiation in the furnace atmosphere by the species.

In particular the apparatus may be used for measuring a concentration of sodium in a portion of the atmosphere of a glass making furnace.

Preferably the collection means and/or the coupling means comprises one or more optical fibre.

Preferably the collection means and/or the coupling means comprises one or more mirror.

Preferably the coupling means comprises a jacket for interfacing with a hole in a wall or roof section of the furnace.

Preferably the apparatus comprises cooling means for cooling the collection means and/or the coupling means.

Preferably the cooling means comprises one or more electrical cooler, in particular a Peltier cooler.

Preferably the cooling means comprises one or more fluid coolant.

Preferably the cooling means comprises at least one water cooling circuit.

Preferably the cooling means comprises at least one air purge.

Preferably the measuring means comprises a spectrometer.

The measuring means is suitably selected to the measure the absorption of electromagnetic radiation in the furnace atmosphere by the species. For example, if the species in the furnace atmosphere absorb visible light, a detector capable of measuring in the visible region of the electromagnetic spectrum is used.

Preferably the measuring means is sensitive to electromagnetic radiation having a wavelength between 380 nm and 800 nm.

Preferably the species is a metal species, preferably an alkali metal species, more preferably sodium.

BRIEF DESCRIPTION OF THE DRAWINGS

The invention will now be described with reference to the following figures.

DETAILED DESCRIPTION OF THE INVENTION

Figure 1:
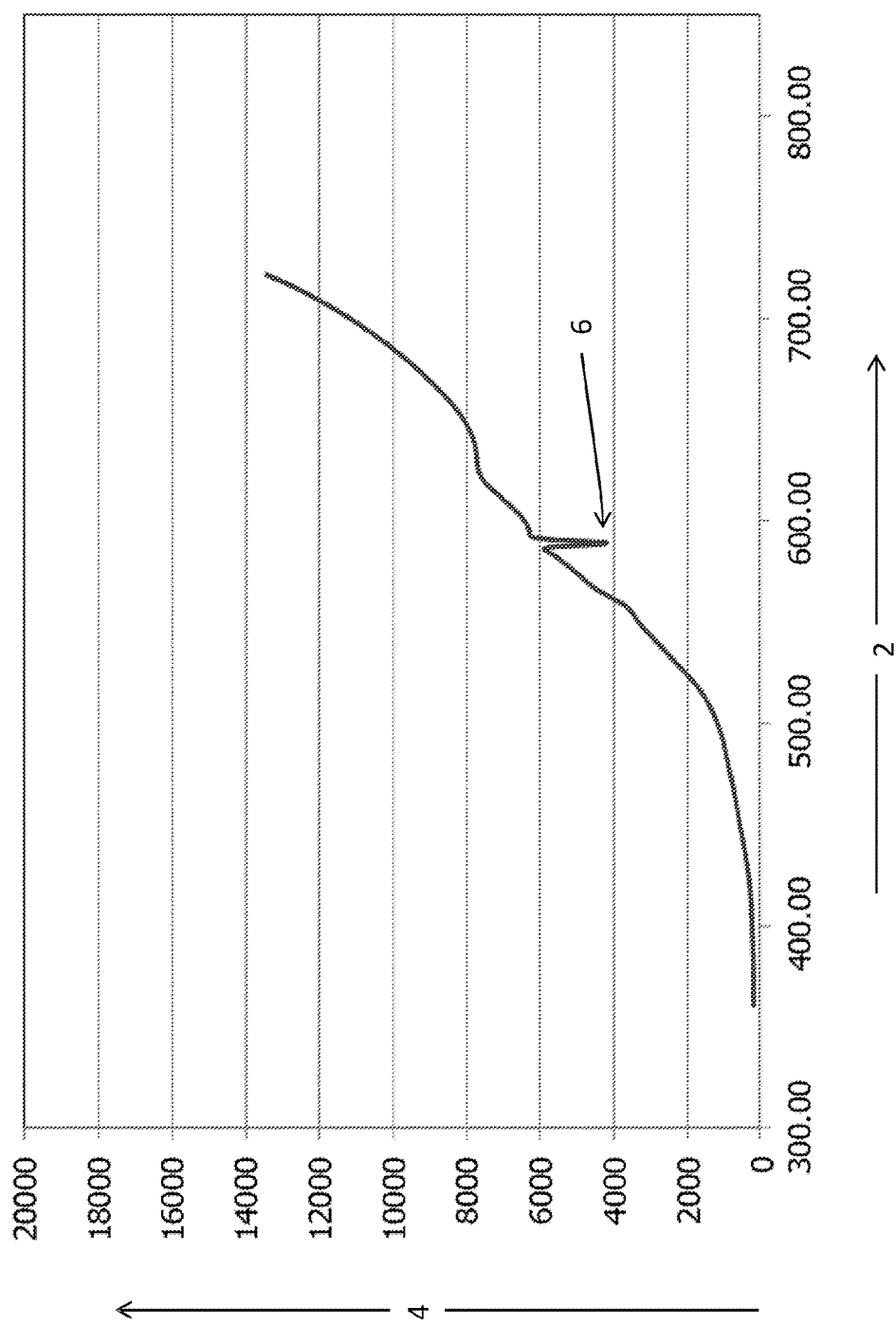
FIG. 1 shows a spectral distribution from inside a float glass making furnace.

FIG. 1 shows the spectral distribution in the refiner end of a float glass making furnace. The temperature at the measuring position is around 1400° C. Axis 2 is the wavelength in nm, and axis 4 is the measured power in watts (W). As can be seen there is an absorption 6 due to sodium atoms in the atmosphere at around 589.5 nm.

Up to around 600 nm to 640 nm, there is reasonable agreement between the spectrum that is measured and that which is calculated from Planck's Law (other than the absorption around 589.5 nm due to sodium in the furnace atmosphere).

Figure 2:
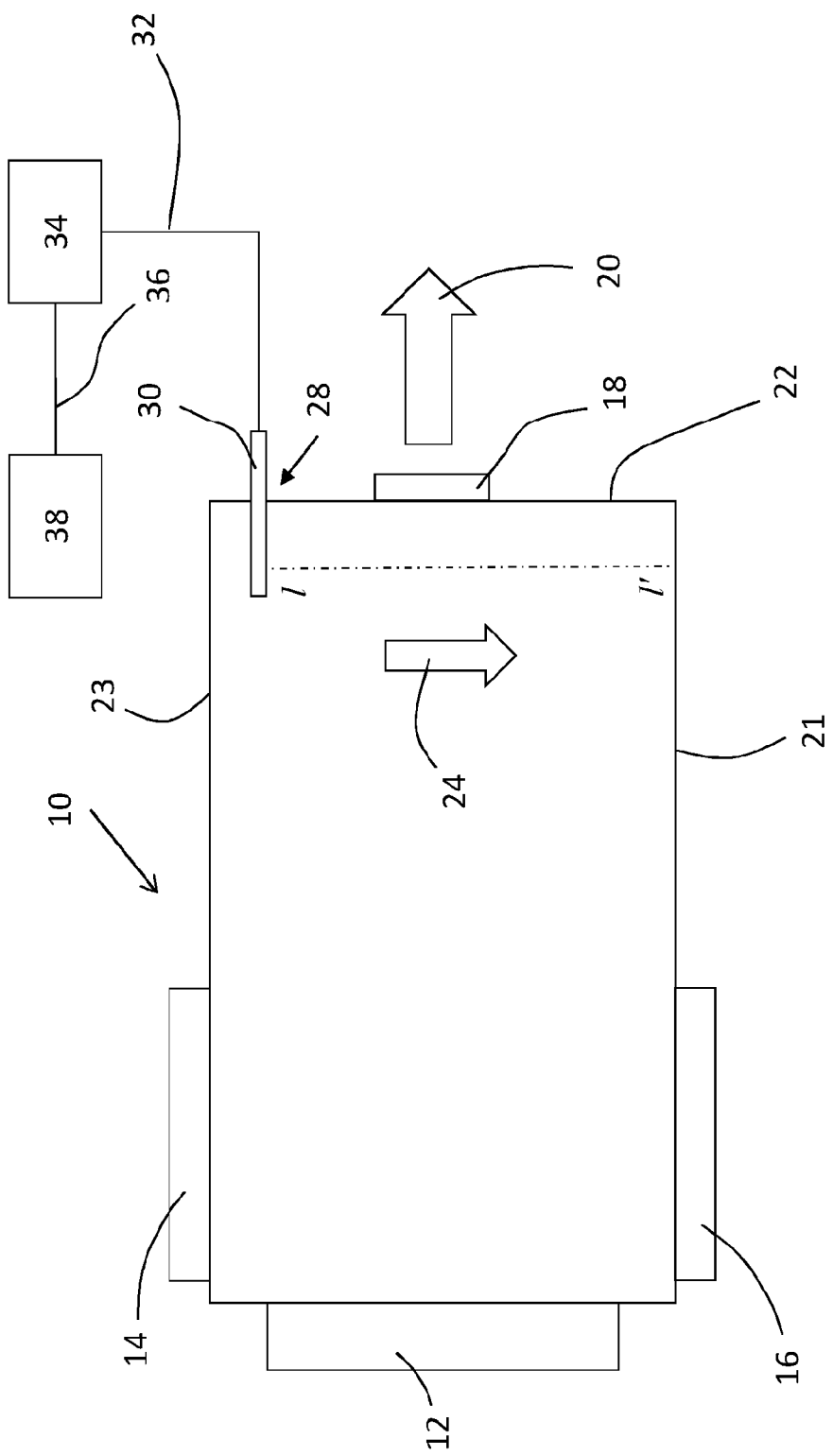
FIG. 2 shows a schematic representation of a furnace showing a measurement position for measuring the intensity of electromagnetic radiation inside the furnace.

FIG. 2 shows a schematic representation of a glass making furnace to show the location of the measurement probe for making measurements of the intensity of visible light inside the furnace.

The glass making furnace 10 has a feed end 12 in which glass making raw materials are fed into the furnace 10 for conversion into molten glass. The furnace has a first burner section 14 and a second burner section 16 for providing the necessary heat into the raw materials for conversion to molten glass. The molten glass exits the furnace through outlet 18 and travels in the direction of arrow 20 to other parts of the glass making furnace, for example a float bath, rollers or container mould.

The furnace 10 has a rectangular configuration with two substantially parallel side walls 21, 23 substantially parallel to the direction of arrow 20. At the outlet end is an end wall 22. The furnace has a bottom and a roof (both not shown). All the walls/roof/bottom are made of suitable refractory materials. Furnaces for making/processing other materials have a similar construction.

Located in a hole in the end wall 22 of the furnace 10 is a suitably water cooled jacket 30. The water cooled jacket 30 is an elongate tubular member that houses an optical fibre suitably configured to view across the furnace in the direction of the arrow 24 along the line l-l'. That is, the optical fibre in the water cooled jacket 30 is configured to receive electromagnetic radiation i.e. visible light from within the furnace that travels along the measurement path length l-l' counter to the direction of arrow 24. The water cooled jacket may include an air purge and/or Peltier cooler for additional cooling. The direction 24 may be substantially parallel to the end wall 22 or at an angle thereto, in particular perpendicular thereto.

The optical fibre 32 is coupled to a suitable spectrometer 34, for example a Thorlab CSS 100 (commercially available from www.thorlabs.de).

The wavelength dependent intensity response of the spectrometer may be calibrated by measuring the intensity response to a calibrated black body source at different temperatures.

The spectrometer 34 is in electrical communication with computer 38 via a suitable cable 36. The computer 38 may also be used to control the spectrometer 34 and exchange data therewith. The computer 38 is used to calculate the sodium concentration in the atmosphere of the furnace 10 based on the wavelength dependent intensity measurements made by the spectrometer 34.

In this particular example the furnace 10 was a float glass making furnace and the water cooled jacket was located in the refiner end of the furnace. The temperature in this region is around 1400-1500° C.

Light from inside the furnace 10 is collected by the suitably configured optical fibre located in the water cooled jacket 30, the optical fibre being suitably coupled to the spectrometer 34.

The spectrometer is used to measure the intensity of light at two wavelengths, 572 nm and 582 nm. It is possible to measure across a wavelength range and to use two wavelengths of interest. It is possible to use more than two wavelengths. Preferably the intensity at each of the two wavelengths is measured at the same time, although they could be measured one after the other.

In a variant to the arrangement shown in FIG. 2, the water cooled jacket 30 may be located in a hole in the sidewall 23, such that the water cooled jacket is substantially perpendicular to the sidewall 23. The optical fibre may be configured to collect light from within the furnace in a direction parallel to the longitudinal axis of the water cooled jacket, and not in a direction perpendicular to the longitudinal axis of the water cooled jacket as shown in FIG. 2. That is, the water cooled jacket may be located in a hole in the sidewall 23 and the optical fibre may be arranged to view across the furnace in the direction of arrow 24.

In another variant, light from inside the furnace exits a hole in one of the furnace walls, for example the sidewall or end wall or roof, and is guided via suitably positioned mirrors and/or lenses for coupling to the spectrometer.

Figure 3:
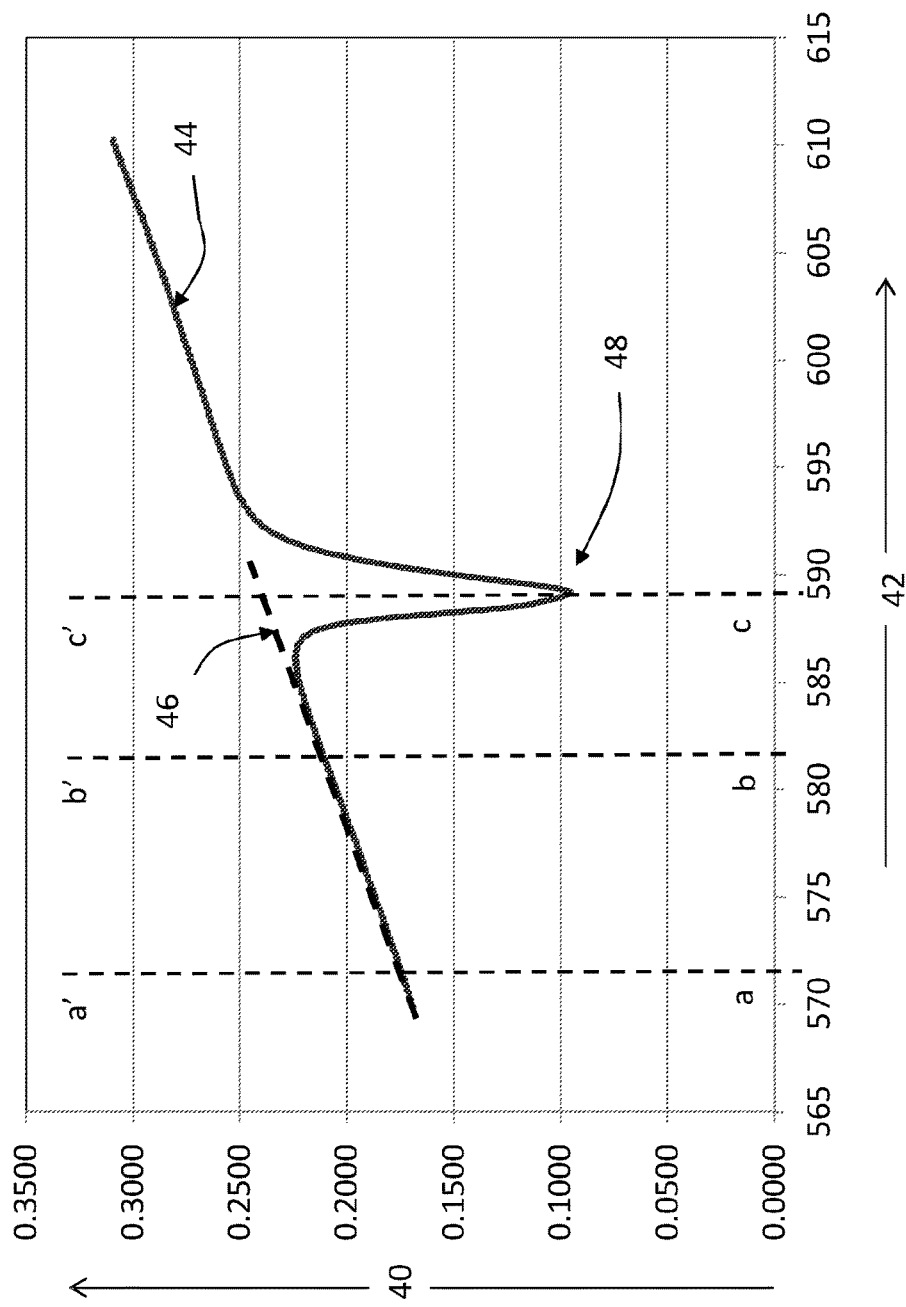
FIG. 3 shows the intensity variation with wavelength for light inside the furnace.

FIG. 3 shows the intensity spectrum for a measurement of electromagnetic radiation inside the furnace 10. The axis 40 is the intensity and the axis 42 is the wavelength in nm.

The intensity variation with wavelength across the region 570 nm to 610 nm, shown as line 44, was measured using a Thorlab CSS-100 spectrometer.

As can be seen in FIG. 3, the absorption due to sodium atoms in the furnace atmosphere is clearly visible at about 589 nm.

The intensity at 572 nm (dotted line a-a') and 582 nm (dotted line b-b') was used to determine an intensity at 589 nm (dotted line c-c') absent any absorbing species at 589 nm.

The wavelength of 589 nm is representative of the wavelength at which elemental sodium atoms absorb visible electromagnetic radiation.

The predicted intensity at 589 nm was determined by interpolation from the measured intensities at 572 nm and 582 nm. The interpolation may be based on the Plank equation, or some other algorithm using the measured intensities. More than two measured intensities may be used in the interpolation to obtain the intensity at 589 nm absent any absorbing species.

In the example shown in FIG. 3, linear interpolation (dashed line 46) was used to determine an intensity at 589 nm. The intensity at 589 nm determined in this way is an estimate of the intensity at 589 nm without there being any absorption due to sodium atoms in the furnace atmosphere (or at least in the portion of the furnace atmosphere under investigation).

Having used the measured intensities to determine an estimated intensity at 589 nm without any sodium atoms in the furnace atmosphere, this is then compared with the actual measured intensity at 589 nm, clearly seen as trough 48 in FIG. 3. The absorption due to sodium atoms is then determined by subtraction i.e. the measured intensity at 589 nm is subtracted from the estimated intensity at 589 nm to give a difference $\delta I_{589\ nm}$.

The difference $\delta I_{589\ nm}$ is a measure of the absorption due to sodium atoms in the furnace atmosphere at the measuring position 28 (with reference to FIG. 2) i.e. $\delta I_{589\ nm}$ is proportional to the concentration of sodium atoms in the portion of the furnace atmosphere under investigation.

It will be evident that the absorption of light in the 589 nm region due to sodium atoms will also depend upon the measurement path length, i.e. essentially the distance in metres between the measuring point 28 and the sidewall 21 (shown as line l-l' in FIG. 2). It is possible to correct the absorption intensity for the measurement path length by assuming the absorption follows the well-known Lambert-Beer Law. Although the Lambert-Beer Law only holds for homogeneous media, in the present method the correction for the measurement path length using the Lambert-Beer Law is acceptable for practical purposes.

It is possible to use a more complex analysis to correct for path length if necessary.

The intensity difference $\delta I_{589\ nm}$ corrected for the measurement path length is also proportional to the concentration of sodium atoms in the portion of the furnace atmosphere under investigation.

To obtain the concentration of sodium atoms in the portion of the furnace atmosphere under investigation the difference $\delta I_{589\ nm}$ is corrected for path length using the well-known Lambert-Law and the quantity so determined can be divided by the absorption coefficient for sodium atoms at 589 nm. A spectrometer calibrated absorption coefficient at 589 nm of 0.01 was used for sodium atoms.

The total sodium concentration in the furnace atmosphere includes contributions from sodium atoms and sodium hydroxide. The ratio of sodium to sodium hydroxide is temperature dependent and can be determined based on thermodynamic calculations. Such calculations are known to a person skilled in the art.

Given that the absorption at 589 nm is due only to the sodium atoms, to get an actual measurement of the total concentration of sodium species in the atmosphere it is necessary to determine the concentration of all sodium species. Practically, only sodium hydroxide was considered as another sodium species in the furnace atmosphere.

Using thermodynamic considerations it was possible to estimate the ratio of sodium to sodium hydroxide at a given temperature in gaseous form. Such calculations showed that the sodium hydroxide to sodium ratio varied between 20:1 at 1500° C. and 10:1 at 1600° C.

By assuming a spectrometer calibrated absorption coefficient at 589 nm of 0.01 for sodium atoms, and a ratio of sodium to sodium hydroxide of 0.05, it was possible to compare the total sodium concentration in the atmosphere determined using a method according to the present invention with a conventional extractive method.

Figure 4:
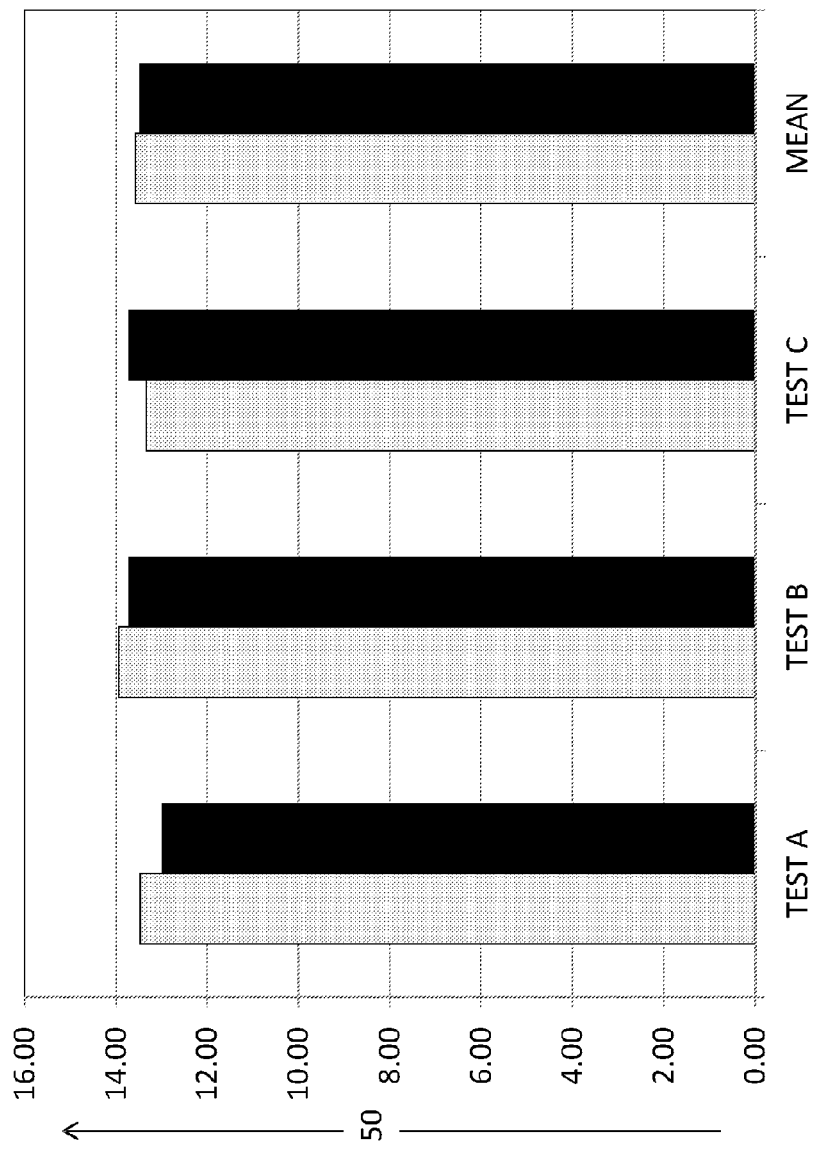
FIG. 4 shows a comparison of the total sodium concentration determined using a method according to the present invention compared with a conventional extractive technique.

FIG. 4 shows the total sodium concentration (in ppm) for three measurements, TEST A, TEST B and TEST C determined using a conventional extractive technique and a method according to the present invention. The average of the three tests is labelled "MEAN". Axis 50 on FIG. 4 is the total sodium concentration in ppm.

A conventional extractive technique was used as follows. A sample was extracted from the furnace atmosphere in the vicinity of the measuring position 28 over a period of twenty minutes and the sodium content determined using well known wet chemical techniques. The results are shown as the dark columns in FIG. 4.

The spectrometer was used to collect wavelength dependent intensity data over each extraction period and subsequently averaged. For each TEST A, B, C, the intensity data at two wavelengths 572 nm and 582 nm was used to linearly interpolate a predicted intensity at 589 nm. The measured intensity at 589 nm was then subtracted from the measured intensity at 589 nm. This intensity difference $\delta I_{589\ nm}$ was then corrected for the measurement path length using the known position of the water cooled jacket 30 relative to the side wall 21.

To obtain a total sodium concentration in the portion of the furnace atmosphere under investigation, the intensity data corrected for measurement path length was then divided by the absorption coefficient for sodium atoms at 589 nm. A spectrometer calibrated absorption coefficient of 0.01 was used. Finally, it was assumed that the ratio of sodium to sodium hydroxide was 0.05 at the measurement temperature of around 1500° C.

As FIG. 4 shows, in view of the number of assumptions and simplifications, the variation in the total sodium concentration measured using the extractive technique (the darker columns in FIG. 4) and the method according to the present invention (the lighter columns in FIG. 4) varied by less than 1 ppm. Typically the difference was within 3 ppm of the total sodium content determined by the conventional extractive technique.

It will be readily apparent that the measuring position could be at any position within the furnace, such as in the burner sections 12, 14 or in the furnace roof The temperature at the other measuring positions may be different.

There may be more than one measuring point such that the variation of sodium in the furnace atmosphere at different locations in the furnace can be determined, each measurement being used to determine the sodium concentration in a portion of the furnace atmosphere.

In the present example a float glass making furnace was used, but the method is applicable to other glass making furnaces, such as those making rolled glass, glass for containers and glass sheets for substrates. Also the method is applicable to other furnaces where it is desirable to measure the sodium content of the furnace atmosphere. The method may also be used for other species that absorb electromagnetic radiation inside the furnace.

The invention claimed is:

1. A method of determining the concentration of a species in a portion of a furnace atmosphere comprising the steps:

(i) measuring a first intensity $I_1$ of electromagnetic radiation in the furnace at a first wavelength $\lambda_1$;

(ii) measuring a second intensity $I_2$ of electromagnetic radiation in the furnace at a second wavelength $\lambda_2$;

(iii) measuring a third intensity $I_3$ of electromagnetic radiation in the furnace at a third wavelength $\lambda_3$, the third wavelength being selected to be representative of the absorption of electromagnetic radiation by the species;

(iv) calculating a fourth intensity $I_4$ at the third wavelength using the first and second intensities, the fourth intensity being an estimate of the intensity of electromagnetic radiation in the furnace at the third wavelength absent any absorbing species in the furnace atmosphere; and (v) using the third intensity and the fourth intensity to determine a parameter that is proportional to the concentration of absorbing species in the portion of the furnace atmosphere.

2. The method according to claim 1, wherein at step (v) the parameter is determined using the difference between the third intensity and the fourth intensity.

3. The method according to claim 1, wherein the measurement steps (i), (ii) and (iii) measure the respective intensity through a measurement path length and wherein the parameter or the third and fourth intensities are corrected for the measurement path length.

4. The method according to claim 1, wherein the measurement steps (i), (ii) and (iii) measure the respective intensity through a measurement path length and wherein the first intensity, the second intensity and the third intensity are corrected for the measurement path length.

5. The method according to claim 1, wherein the parameter is used to determine a concentration of the species in the portion of the furnace atmosphere.

6. The method according to claim 5, wherein the concentration is a qualitative concentration of the species in the portion of the furnace atmosphere or a quantitative concentration of the species in the portion of the furnace atmosphere.

7. The method according to claim 5, wherein the parameter is used to determine the quantitative concentration of the species in the portion of the furnace atmosphere by using an absorption coefficient for the particular species at the third wavelength, the absorption coefficient indicating the absorption strength of a unit quantity of the species per unit length.

8. The method according to claim 1, wherein the first and second intensities ($I_1$, $I_2$) are used to determine the temperature inside the furnace, the temperature being determined by calculating the gradient $\delta I/\delta \lambda$ and comparing the calculated gradient with the theoretical gradient at that wavelength, the determined temperature in the furnace then being used to calculate a blackbody spectrum, thereby allowing a calculation of an intensity at the third wavelength.

9. The method according to claim 1, wherein the fourth intensity is calculated by linear interpolation between the first intensity at the first wavelength and the second intensity at the second wavelength to obtain a predicted intensity at the third wavelength.

10. The method according to claim 1, wherein the first wavelength and the second wavelength are shorter than the third wavelength.

11. The method according to claim 1, wherein the first wavelength is shorter than the third wavelength and the second wavelength is longer than the third wavelength.

12. The method according to claim 1, wherein the species is sodium.

13. The method according to claim 12, wherein the third wavelength is between 585 nm and 595 nm.

14. The method according to claim 12, wherein the first wavelength is between 500 nm and 584.9 nm.

15. The method according to claim 12, wherein the second wavelength is between 500 nm and 584.9 nm or wherein the second wavelength is between 596 nm and 700 nm.

16. The method according to claim 1, wherein the measured intensity at more than two wavelengths is used to determine the intensity at the third wavelength.

17. The method according to claim 1, wherein the furnace is a glass making furnace.

18. Apparatus for measuring the concentration of a species in a portion of a furnace atmosphere, the species absorbing electromagnetic radiation in the furnace, the apparatus comprising:
   means for collecting electromagnetic radiation to collect electromagnetic radiation from inside the furnace;
   means for coupling to direct the collected electromagnetic radiation to a suitable means for measuring, the means for measuring being configured to:
     (i) measure a first intensity $I_1$ of electromagnetic radiation in the furnace at a first wavelength $\lambda_2$;
     (ii) measure a second intensity $I_2$ of electromagnetic radiation in the furnace at a second wavelength$\lambda_2$;
     (iii) and measure a third intensity $I_3$ of electromagnetic radiation in the furnace at a third wavelength $\lambda_3$, the third wavelength being selected to be representative of the absorption of electromagnetic radiation by the species; and
   means for computing, configured to take the output from the measuring means to determine the amount of absorption of electromagnetic radiation inside the furnace at a measurement wavelength, the measurement wavelength being selected to be representative of the absorption of electromagnetic radiation in the furnace atmosphere by the species, by
   calculating a fourth intensity $I_4$ at the third wavelength using the first and second intensities, the fourth intensity being an estimate of the intensity of electromagnetic radiation in the furnace at the third wavelength absent any absorbing species in the furnace atmosphere; and
   using the third intensity and the fourth intensity to determine a parameter that is proportional to the concentration of absorbing species in the portion of the furnace atmosphere.

19. The apparatus according to claim 18, wherein:
   the means for measuring is sensitive to electromagnetic radiation having a wavelength between 380 nm and 800 nm; or
   wherein the species is a metal species.

20. A method of determining the concentration of a species in a portion of a furnace atmosphere without using a separate background trace, comprising the steps:
   (i) measuring a first intensity $I_1$ of electromagnetic radiation in the furnace at a first wavelength $\lambda_1$ ;
   (ii) measuring a second intensity $I_2$ of electromagnetic radiation in the furnace at a second wavelength $\lambda_2$;
   (iii) measuring a third intensity $I_3$ of electromagnetic radiation in the furnace at a third wavelength $\lambda_3$, the third wavelength being selected to be representative of the absorption of electromagnetic radiation by the species;
   (iv) calculating a fourth intensity $I_4$ at the third wavelength using the first and second intensities, the fourth intensity being an estimate of the intensity of electromagnetic radiation in the furnace at the third wavelength absent any absorbing species in the furnace atmosphere; and
   (v) using the third intensity and the fourth intensity to determine a parameter that is proportional to the concentration of absorbing species in the portion of the furnace atmosphere.

* * * * *

UNITED STATES PATENT AND TRADEMARK OFFICE
CERTIFICATE OF CORRECTION

PATENT NO. : 10,345,229 B2  Page 1 of 1
APPLICATION NO. : 15/506276
DATED : July 9, 2019
INVENTOR(S) : Michael Richard Haden et al.

It is certified that error appears in the above-identified patent and that said Letters Patent is hereby corrected as shown below:

In the Claims

Column 11, Line 25, after the phrase "first wavelength $\lambda$" the "$_2$" should read "$_1$".

Signed and Sealed this
Twenty-second Day of October, 2019

Andrei Iancu
*Director of the United States Patent and Trademark Office*